United States Patent [19]
Stowell

[11] 3,968,310
[45] July 6, 1976

[54] HALF-ESTER REACTION PRODUCTS OF MALEATED ALPHA-OLEFINS AND MONOHYDRIC ALCOHOLS

[75] Inventor: James K. Stowell, Decatur, Ill.

[73] Assignee: A. E. Staley Manufacturing Company, Decatur, Ill.

[22] Filed: Mar. 14, 1974

[21] Appl. No.: 451,662

[52] U.S. Cl. ............................... 428/411; 156/325; 260/31.8 M; 260/31.8 N; 260/31.8 HR; 260/31.8 R; 260/31.8 PQ; 260/31.8 AN; 260/31.8 L; 260/485 P
[51] Int. Cl.² .......................................... B32B 9/04
[58] Field of Search ................. 260/31.8 R, 31.8 M, 260/31.8 N, 31.8 HR, 31.8 PQ, 31.8 AN, 31.8 L, 485 P; 428/411; 156/325

[56] References Cited
UNITED STATES PATENTS

| | | | |
|---|---|---|---|
| 2,380,699 | 7/1945 | Kyrides | 260/485 P |
| 3,345,320 | 10/1967 | Uffner et al. | 260/31.8 R X |
| 3,378,509 | 4/1968 | Jerabek | 260/31.8 R X |

Primary Examiner—Lewis T. Jacobs
Attorney, Agent, or Firm—M. Paul Hendrickson; Charles J. Meyerson

[57] ABSTRACT

Half-ester reaction products possessing unique adhesive properties are obtained by reacting maleated alpha-olefins with hydrocarbylpolyoxyalkylenealkanols. The half-ester in combination with other thermoplastic materials provide improved hot-melt formulations. Paper stocks contaminated with these hot-melt formulations can be recycled into a high grade paper pulp by conventional alkaline repulping processes. The half-ester products are also useful as a solvent in thermoplastic polymerization processes.

20 Claims, No Drawings

HALF-ESTER REACTION PRODUCTS OF MALEATED ALPHA-OLEFINS AND MONOHYDRIC ALCOHOLS

BACKGROUND OF THE INVENTION

Within recent years, a world-wide scarcity of natural resources has become a reality. This scarcity has made it necessary to recycle scrap articles and reuse them as raw materials. Within recent years, recycled paper stock has become increasingly important to the paper industry. Unfortunately, the recycling of a high-grade paper stock pulp is often frustrated by fabricating materials which were previously employed in their manufacture. Water-insoluble, hot-melt adhesives (such as presently employed in the manufacture of corrugated, cardboard, bags, books, etc.) are typical fabricating materials which cannot be effectively and economically removed from the recycled paper stock. Scrap paper articles contaminated with these water-insoluble, hot-melt adhesives are usually disposed of as wastes or employed in very low quality paper articles.

To be suitably adapted for its intended use, a hot-melt adhesive should possess a plurality of prerequisital properties. In general, the hot-melt adhesives should have: a relatively high melting point, sufficient flow characteristics to be effectively deposited upon the paper stock, suitably adapted to high speed fabrication equipment such as presently employed in the industry, compatibility and adhesiveness to the paper stock and have a relatively short set period. Such paper stock containers also necessitate an adhesive bond which can withstand a broad spectrum of physical, environmental and chemical abuses such as normally encountered during the shipment and storage thereof. Such containers are frequently exposed to a host of physical stresses (e.g., tearing, shearing, compression, impact, tension, etc.). The hot-melt adhesive should have sufficient durability to withstand these physical abuses. Divergent environmental conditions such as normally encountered by their usage in the trade also place further performance demands upon the required functional attributes of these adhesives. The hot-melts are normally required to retain their functional attributes under diverent humidity and thermal conditions (e.g., sub-zero to tropical, and arid to extremely humid conditions). The packaged contents as well as environmental conditions necessitate a hot-melt adhesive formulation which possesses adequate resistance against chemical degradation.

In U.S. Pat. No. 3,753,944 by J. Sirota et al., water-soluble, hot-melt adhesives comprised of blends of polyethylene oxides and polyalkylene oxides are disclosed. British Pat. No. 1,291,016 discloses a hot-melt adhesive comprised of a tall oil resin and/or colophony resins with surface-active polyethylene oxide adducts having an HLB Griffin value of 10-20. As in U.S. Pat. No. 3,753,944, the British patent discloses these water-soluble, hot-melt adhesives as being easily removable with water. As a result, these water-soluble, hot-melt adhesives are generally employed for highly specific end uses. The water-soluble, hot-melt adhesives, however, are not deemed to be a suitable replacement for the insoluble adhesives because of their inherent instability under humid, wet or inclement conditions.

Heretofore the art has been relatively successful in providing the trade with hot-melt hot-mel adhesives which meet the aforementioned physical and chemical requirements. In fulfilling these requirements, the commercially available, water-insoluble, hot-melt adhesives inherently impair effective recovery of high grade paper pulp stocks from paper scraps contaminated therewith. A water-insoluble, hot-melt adhesive which could be effectively and economically removed from scrap paper stock under existing alkali repulping technology would provide an additional, high-grade paper pulp source for the trade. A need also exists for insoluble, hot-melt additive compositions which can be readily converted to a water-soluble salt form and thus fulfill the aforementioned specialty uses. Such a hot-melt additive would possess a dual functionality heretofore not feasible with the existing hot-melt additives.

OBJECTS

It is an object of the present invention to provide a novel composition which is characterized as being hydrophobic at neutral and acidic pH's, but which can be converted to a hydrophilic form by alkaline treatment thereof.

Another object of the invention is to provide a composition suitable for use as a hot-melt additive and hot-melt adhesive compositions containing the same.

An additional object of the invention is to provide an alkali, repulpable paper stock material containing an adhesive which is soluble in aqueous alkaline mediums.

Another object of the invention is to provide a process for laminating substrates with a novel hot-melt composition and the laminates thereof.

A still further object is to provide an improved method for preparing thermoplastic products in the presence of hydrocarbylpolyoxyalkylene esters.

DESCRIPTION OF THE INVENTION

In accordance with the present invention there is provided a composition represented by the following Formula I:

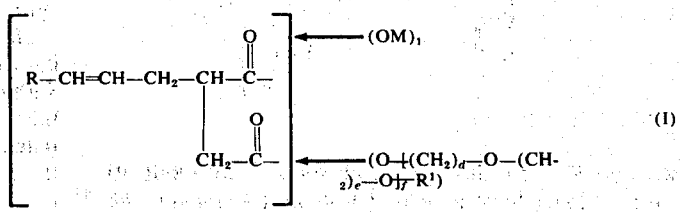

wherein R and $R^1$ represent a hydrocarbyl group (free from ethylenical unsaturation), d and e represent integers having a value of 2–5 inclusive, $f$ is an integer from about 2 to about 1000 or more and M is cation (i.e., metal cations, nitrogen based cations or hydrogen). The polyalkylene oxide units may be the same or a mixture of different alkylene oxides (i.e., d and e, can represent identical or different values throughout the alkylene oxide chain). The Formula I composition wherein $f$ is an integer (e.g., about 5 to 50), d and e represent methylene groupings of 2 to 3 carbon atoms inclusive, $R^1$ represents an $A—(R^2)_g$ moiety with A being a phenylene or phenenyl group with $R^2$ representing alkyl moiety or dialkyl moieties, each of which have about 5 to 30 carbon atoms inclusive (advantageously of 7 to 15 carbon atoms inclusive) and $g$ is an integer of 1 or 2, have been found to be particularly useful as hot-melt adhesive additives. As evident from Formula I, the compositions of the present invention have both hydrophilic and hydrophobic groups. At neutral and acidic pH's, the above compositions which contain the carboxylic acid moiety are characterized as being insoluble in aqueous mediums. The salts thereof are generally characterized as hydrophilic and dispersible in natural and basic aqueous solutions.

The composition represented by Formula I can be conveniently prepared by initially reacting an alpha-olefin with maleic anhydride to provide a maleated alpha-olefin and thereafter reacting the maleated alpha-olefin with a hydrocarbylpolyoxyalkylenealkanol to provide the Formula I composition.

Maleation of alpha-olefins is well known to the art. The reaction between maleic anhydrides (B) and alpha-olefins (A) herein is illustrated by the following equation (II):

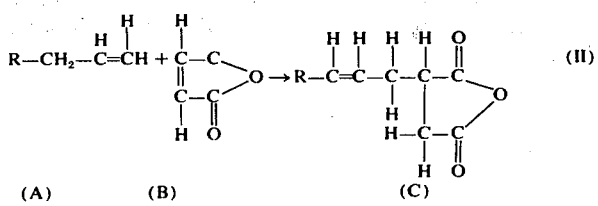

(A)   (B)   (C)

wherein R is an alkyl group of about 5 to about 30 carbon atoms. Illustrative alpha-olefins (A) include the branched and straight chain monoethylenically unsaturated olefins such as: 1-heptene; 2,4,4-trimethylpentene-1; 1-octene; 1-nonene, 1-decene; 1-undecene; 1-dodecene, 1-tridecene; 1-tetradecene, 1-pentadecene, 1-hexadecene: 1-heptdecene; 1-octodecene; 1-eicosene: 1-hepteicosene: 5-methyl-1-hexene: mixtures thereof and the like. The chain length of the R group will have an effect upon the hydrophilic or hydrophobic properties of the reaction product (C) provided herein. The short-chain alkyl groups are more hydrophilic than those of a longer chain length. If it is desired to utilize the reaction product in water-insoluble, hot-melt formulations, improved hot-melt properties are achieved when alpha-olefins of about $C_8$ to about $C_{20}$ (preferably $C_{10}$ to $C_{15}$) are employed as reactant A.

In preparing the compositions represented by Formula I, the maleated alpha-olefins (C) are then reacted with a hydrocarbylpolyoxyalkylenealkanol (D) as illustrated by Equation III.

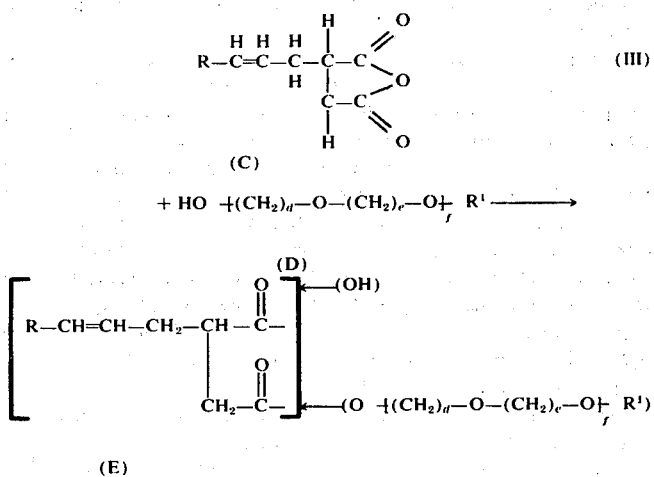

wherein $d$, $e$, $f$, R and $R^1$ are integers and groups as defined above.

The aforementioned hydrocarbylpolyoxyalkylenealkanol reactants (D) and their preparation are known to the art. Alkylarylpolyoxyalkylenealkanols are commercially available and frequently utilized as nonionic surfactants. These monohydric alcohols can be conveniently prepared by reacting the appropriate alkyl phenol with an alkylene oxide. Monohydric alcohol reactants (D) wherein the phenoxy group has mono- or di-, long-chain alkyl groups of about 6 to about 20 carbon atoms (preferably between 7 and 12), the polyoxypropylene and/or polyoxyethylene of about 10 to about 50 average alkyleneoxide units (preferably about 20 to about 40) with terminal ethanol and/or propanol groups are particularly useful reactants (D) in preparing reaction product (E). Representative examples of preferred reactants (D) include the heptylphenoxypolyethoxyethanols, octylphenoxypolyethoxyethanols, methyloctylphenoxypolyethoxyethanols, nonylphenoxypolyethoxyethanols, dodecylphenoxypolyethoxyethanols.

The reactants proceed to completion without requiring catalysts or solvents to assist the reaction thereof. Although the reaction can be conducted at temperatures between the melting point of the reactants and reaction product, it is most suitably conducted at temperatures above 100°C. and under anhydrous or substantially anhydrous conditions with uniform mixing of the reaction media until completion thereof. In general these elevated temperatures accelerate the reaction rate and provide a means for maintaining the reaction mass under a substantially anhydrous state.

In the partial esterification process, the partial esterification of the anhydride moiety may be conducted in the presence of the monohydric alcohol reactant (D) and the maleated alpha-olefin (C) as the sole reaction media ingredients. The reactants (C) and (D) are most suitably provided in the reactor essentially free from contaminants which would adversely affect the partial esterification thereof. However, if desired, the partial esterification can be carried out in conjunction with organic solvents, catalysts or other partial esterification aids provided they do not adversely affect the partial esterification reaction.

The partial ester preparation is advantageously conducted by employing the appropriate amount of reactants and conducted under esterification conditions sufficient to provide the desired partial ester reaction product in a form essentially free from contamination. Excessive amounts of alcohol reactants can result in diester formation. An insufficient amount of alcohol will result in incomplete conversion of the maleic anhydride to the half-ester product. The reaction is preferably conducted for a period of time sufficient to provide the half-ester product which is essentially free from diester and unreacted reactant contaminants. Accordingly, the reaction is most preferably conducted by employing approximately equivalent molar concentrations of the monohydric alcohol reactant and the maleated alpha-olefin reactant and thus obtain the half-ester product.

The partial ester reaction products of this invention can easily be prepared by initially converting the hydrocarbylpolyalkyleneoxidealkanol to a molten form followed by the addition (either incrementally, continuously or in a single stage) of the maleated alpha-olefin under sufficient mixing conditions to provide a homogeneous, molten reaction media thereof. In most instances, the monohydric alcohol reactants, employed herein, are solids and have melting points between about 30° to 80°C. Temperatures ranging from about 50° to about 200°C. (preferably about 100° to about 150°C.) for about 1 to about 5 hours (preferably about 2–3 hours) are generally sufficient to complete the reaction thereof.

Since the Equation III reaction reactants are readily reactive with one another and the reaction thereof proceeds to the desired reaction product without requiring reaction media processing aids or contaminants, the resultant reaction product (E) can be obtained in a form essentially free from contaminants and may be directly recovered from the reactant without additional processing thereof.

In general, reaction products (E) are hydrophobic and will have melting points of about 40° to about 80°C. Reaction product (E) can be converted, if desired, to a water-soluble form by reacting the carboxylic acid moieties thereof with an aqueous base. Illustrative bases for converting the reaction product (E) to a water-soluble salt include the alkali hydroxides (e.g., sodium, potassium, lithium hydroxides, etc.), and nitrogen bases. Typical nitrogen bases include ammonia, ammonium hydroxide, primary and secondary amines such as the methylamines; ethylamines, propylamines; 3-methoxypropylamine; monoethanolamine; diethanolamine; 2-amino, 2-methyl, 1-propanol; 2,amino, 2-methyl-1,2-propanediol; 2-(methyl amino)-ethanol; 2-amino-2-methyl-1,3-propanediol; morpholine; tertiary amines such as trimethylamine; triethylamine; tripropylamine; diethyl methyl amine; trihexylamine; tributylamine; triethanol and tributanol amines; dimethyl and diethyl monoethanol amines; other nitrogen bases such as trimethylbenzyl ammonium hydroxide; triethylbenzyl ammonium hydroxide; N-ethyl piperidine; N-methyl pyrrolidone; N,N-dimethyl-2-ethylhexylamine; N-methyl-2-methyl morpholine; etc., mixtures thereof and the like. If desired, the reaction product (E) may be neutralized with polyvalent bases (e.g., alkaline earth hydroxides, etc.) to provide dimers, trimers, tetramers thereof which are covalently bonded to the polyvalent metal cation.

The water-insoluble reaction products of this invention and the salts thereof may be used as hot-melt additives, surface active agents, plasticizers, tackifiers, thickening agents for aqueous and organic systems, a reactant for preparing thermoplastic and thermoset resins, a solvent in the polymerization of polymers, etc. The water-soluble salts of the Formula I composition may be used as a vehicle in aqueous adhesive or aqueous coating formulations. Similarly, if it is desired to have the water-soluble, hot-melt formulation of the type disclosed in U.S. Pat. No. 3,753,944, the compositions of Formula I can be neutralized and converted to a thermally stable, water-soluble salt form (e.g., sodium and potassium salts) and employed as a water-soluble, hot-melt additive. In general, paper stocks adhesively bonded with hot-melt formulations containing the carboxylic acid half-ester of Formula I are sufficiently hydrophobic in character to be useful as a replacement for the insolubles presently employed by the industry. These carboxylic acid half-esters are particularly useful in preparing paper stocks which are adapted for recycling into a high grade of pulp via conventional, alkali repulping processes.

In a more limited aspect of the present invention there is provided adhesive compositions containing the Formula I compositions as an adhesive component. The adhesive additives of this invention possess a plurality of functional attributes. For example, the Formula I composition may be used as an additive to improve upon: the over-all adhesive performance of the final adhesive formulation, the dispersibility of the adhesive formulation components in aqueous or organic based vehicles, the plasticity and flexibility of the adhesive composition (prior, during or after its application), the tack characteristics of the adhesive, the flow and viscosity characteristics of the adhesive composition, the melting properties of the adhesive formulation, etc. Accordingly, the amount of hot-melt additive herein can vary considerably and will depend upon the particular function to be served thereby. For many adhesive formulations, the Formula I composition may amount to only about 0.25% by weight of its total solids content. In other adhesive formulations, it may be desirable to utilize the Formula I composition as a principle or major adhesive binder or even as the sole adhesive component.

The hot-melt additives of this invention are most suitably combined with other thermoplastic polymers. The hot-melt additive may be employed as a partial or complete replacement for conventional, hot-melt plasticizers or tackifiers and thus be used in relatively small amounts (e.g., about 0.5% by weight). Most generally, the hot-melt formulations provided by this invention will have melting points between about 150° and about 350°F. The Brookfield viscosity of these hot-melt formulations will depend primarily upon their intended usage and may range broadly from about 1,000 cps up to about 200,000 cps (at 350°F.). Advantageously the hot-melt formulation provided by the present invention will have a viscosity of less than about 35,000 cps, preferably less than 10,000 cps and more preferably less than about 5,000 cps.

For most commercial applications, about 1 to about 40 parts by weight of conventional thermoplastic materials are combined with each part by weight of the hot-melt additive herein. Advantageously, the hot-melt formulations will contain about 3 to about 15 parts by weight of another conventional thermoplastic material for each part by weight of the hot-melt additive. Advantageously the melting points of these hot-melt formulations will range from about 160° to about 250°F. Hot-melt formulations particularly adapted for use in paper stocks will usually contain from about 10 to about 20% by weight of the hot-melt additives (based upon total thermoplastic material including the hot-melt additive herein) and usually have a melting point of about 175° to about 225°F.

Illustrative hot-melt homopolymers and/or copolymers (water-soluble and/or water-insoluble) include: the vinyl aromatics (e.g., styrene; meta- and para-methyl, ethyl, isopropyl, styrenes; sec- and t-butylstyrenes; p-heptyl and p-(2-ethylhexyl) styrene, p-benzyl and p-cyclohexyl styrene; mono and di-methoxy and ethoxy styrenes as well as the alkyl and alkoxy substituted styrenes; alpha-methyl styrene and derivatives thereof, the halostyrenes (e.g., chlorostyrene, 2,5-dichlorostyrene), the cyano, carboxy-, hydroxy-, nitro and aminostyrenes, vinyl biphenyls, etc.), esters of the alpha-beta ethylenically unsaturated carboxylic acid such as the methacrylate and acrylate esters of methyl, ethyl, isopropyl, and alpha-n-butyl, phenyl, n-hexyl, n-amyl, 2-ethylhexyl, hydroxymethyl, benzyl, hydroxypropyl, nonyl, dodecyl; ethylenically unsaturated carboxylic acid monomers, such as acrylic, methacrylic, itaconic, fumaric, maleic, crotonic as well as the esters and salts thereof; the acrylonitriles and methacrylonitriles; vinylidene cyanide; acrylamide and methacrylamides and corresponding N-substituted amides thereof (N-methyl, N-ethyl, N-n-dodecyl, N,N-diethyl, N-phenyl, N-methyl-, N-phenyl, etc.); vinyl acetate and related monomers (e.g., chloro, methoxy, diethyl, propionate, butyrate, acrylate, methacrylate, oleate); vinyl esters of aromatic acids (e.g., benzoate, alkoxybenzoates, etc.); vinyl halides (e.g., vinyl chloride); vinylidene halides (e.g., chlorides); mono and diethylenically unsaturated hydrocarbons such as ethylene, propylene, isobutylene, amylene, hexene; isoprene, butadiene, bicyloheptadienes, etc.; the alkyl, alicyclic and aralkyl vinyl ethers of methyl, ethyl, propyl, butyl cyclohexyl, p-butylcyclohexyl, phenyl, p-chlorophenyl n-benzyl, nonyl, n-decyl, oleyl, etc., and the like.

Typical prior art, hot-melt thermoplastic materials include polyvinyl acetate and polyethylene blends (e.g., see U.S. Pat. No. 2,772,247 by G. O. Schroeder); polyvinyl alcohol as major thermoplastic with or without polyvinylacetate and other auxiliary components (e.g., see U.S. Pat. Nos. 3,296,018 by Sullivan et al., 3,143,518 by Smith et al. and 3,418,202 by Brunson et al.); polyolefin blends (e.g., U.S. Pat. Nos. 3,478,131 by Wharton et al., 3,370,106 by Hall et al. and 3,201,498 by Brunson et al.), ethylene-vinyl acetate copolymers (e.g., see U.S. Pat. No. 3,419,641 by Peterkin et al.); vinyl methyl ether-maleic anhydride copolymers, vinyl acetate-vinyl pyrrolidone copolymers, polyacrylic acid, polypropylene, vinyl ether and/or isobutyl ether copolymers copolymerized with monomers such as acrylates, acrylonitrile, vinyl esters, methyacrylates, chloroprene, maleic anhydrides, maleates, etc. (e.g., see U.S. Pat. No. 3,462,342 by Cooper et al.); copolyesters of sebacic and terephthalic acids and tetramethylene glycol (e.g., see U.S. Pat. No. 3,374,137 by Wiener); alpha-methyl styrene resins (e.g., see U.S. Pat. Nos. 3,429,843, 3,401,131 and 3,401,132); terpeneureathane resins (e.g., see U.S. Pat. No. 3,463,753), polyoxyalkyleneoxide alcohols and adducts thereof; copolymers of vinyl esters and salts of monoalkyl maleic acid esters (e.g., see U.S. Pat. No. 2,643,238); maleated polyethylene and copolymers of ethylene, alkyl acrylate, alkyl methacrylate or vinylalkonoate (e.g., see U.S. Pat. No. 3,595,943); natural resins such as tall oil or colophony resins and/or ethylene/vinyl acetate copolymers (e.g., see U.S. Pat. No. 3,775,146); the alkali-soluble copolymers of vinyl acetate and polymerizable carboxylic acid monomers, such as vinyl acetate-crotonic acid copolymers, polyvinyl alcohols (e.g., see U.S. Pat. No. 3,220,967); polymerized saturated esters of polyalkylene glycol esterified with dicarboxylic aliphatic acids and vinyl chloride-vinyl acetate copolymers (e.g., see Canadian Pat. No. 527,975) all of which are incorporated herein by reference.

Various other conventional additives such as antioxidants, heat and light stabilizers, dyes, slip agents, nonblocking agents, pigments, plasticizers, viscosity modifiers, tackifiers, fillers, flame retardants, or the like may be added, if desired, as is well known to the art.

When Formula I compositions are to be utilized as coating or adhesive composition in conjunction with other thermoplastic materials, it is desirable to provide a homogeneous blend of these ingredients. This may be accomplished by uniformly and homogeneously admixing a molten mass of the melted Formula I composition with a melt of the desired thermoplastic materials. The homogeneous molten mass may be directly applied to a substrate or solidified and subsequently used as a hot-melt adhesive composition.

Exceptional functional properties for adhesive compositions are achieved when the thermoplastic materials employed in conjunction with the Formula I composition are polymerized in situ with the Formula I components. In this more limited aspect of the invention, the amount of Formula I composition present during the polymerization of the ethylenically unsaturated monomers of the thermoplastic polymers will primarily depend upon its intended functional purpose. If it is desired to utilize the Formula I composition as a surface active agent in the polymerization with other solvent or liquid dispersents, the Formula I composition may be present in the polymerization media in an amount of about 0.1 to about 2% by weight of the total polymerized monomer weight. Somewhat greater amounts (e.g., .25 to about 5%) are usually employed in the polymerization reaction when it is desired to impart improved tack and/or leveling and/or plasticizing properties to the adhesive compositions of this invention.

In this more limited aspect of the invention, it is particularly advantageous to utilize the Formula I composition as a dispersent or codispersent for the in situ polymerization of the ethylenically unsaturated monomers. Although the Formula I composition may be used as a minor polymerization solvent or dispersent, it is particularly advantageous to conduct the polymerization process wherein it comprises at least a major polymerization solvent or dispersent. The polymerization process herein is most suitably adapted for polymerizing ethylenically unsaturated monomers wherein the polymerization solvent or dispersent consists essentially of the Formula I composition.

The polymerization process herein can be employed to prepare a wide range of thermoplastic materials as mentioned hereinbefore. The polymerization process is best adapted to the polymerization of ethylenically unsaturated monomers, including vinyl type monomers, which are uniformly dispersible or soluble in the Formula I compositions. The polymerization reaction is generally conducted in the presence of a sufficient amount of Formula I composition to enable the ethylenically unsaturated monomer to polymerize therein. For most polymerization reactions, about 5 parts by weight or more of the Formula I composition for each 100 parts by weight of polymerized monomers will be employed. Although it is not pragmatic or economical to conduct the polymerization reaction with minute amounts of ethylenically unsaturated monomer, such a reaction can be conducted if desired. The weight ratio of the Formula I composition to the ethylenically unsaturated monomer weight in most polymerization reactions will range from about 1:19 to about 19:1. The resultant polymerization products are particularly useful as hot-melt adhesive compositions. Preferably the polymerization reaction is conducted in the presence of about 3 to about 15 parts by weight ethylenically unsaturated monomer, for each part by weight of the Formula I composition. In the preferred embodiments for preparing hot-melt adhesive compositions herein, the polymerization reaction employs about 4 to about 9 parts by weight of ethylenically unsaturated monomer for each part by weight of the Formula I composition.

The polymerization reaction is generally conducted in the presence of a free-radical catalyst. The catalyst can be soluble in the Formula I composition phase, or the monomeric phase, or both. Among the illustrative polymerization catalysts are the organic peroxides and organic hydroperoxides such as benzoyl peroxide, tertiary butyl hydroperoxide, diisopropyl benzene hydroperoxide, cumene hydroperoxide, caproyl peroxide, methyl ethyl ketone peroxide, mixtures thereof and the like. Other free-radical catalysts can also be used, such as azodiisobutyronitrile, and other aliphatic azo compounds of the type having an acylic azo group and an aliphatic carbon atom on each nitrogen, at least one of which is tertiary. In the polymerization reaction, the particular combination of monomers governs the selection of the catalyst since some monomers respond better to one variety than they do to another. The amount of polymerization catalyst will usually be between about 0.1% to 10% by weight of the total ethylenically unsaturated monomer weight. For most polymerization reactions, the amount of catalyst will range from about 0.5 to about 5% by weight (preferably about 1 to about 3%) of the total polymerized ethylenically unsaturated monomer weight.

The polymerization reaction may be conducted anywhere between the melting point and the boiling point of the polymerization reaction media. Most suitably, the polymerization reaction is conducted at a temperature from about 40° to about 175°C., with a temperature of about 75° to about 150°C. being preferred. As further illustrated by the Examples, the polymerization reaction is most suitably conducted by initially converting the Formula I composition to the molten or liquid state, and thereafter introducing the ethylenically unsaturated monomer and catalyst (if required) into the polymerization reaction media. The polymerization reaction is then conducted in situ until the desired polymerization product is obtained. Pursuant to the present polymerization process a plurality of sequential polymerization reactions may be conducted with the resultant polymerizate containing a multiplicity of different thermoplastic polymeric materials therein. Example I illustrates a two-stage, in situ, polymerization process. The initial polymerization reaction provides a copolymer polymerizate of vinyl acetate and crotonic acid. The second in situ, polymerization reaction provides a vinyl toluene-alpha methyl styrene-methacrylic acid terpolymer. The resultant product is comprised of a homogeneous blend of the thermoplastic copolymer and terpolymer uniformly dispersed within the Formula I composition phase.

The polymerization reaction is generally conducted under mixing means sufficient to provide a homogeneous dispersion of the ethylenically unsaturated monomers in the polymerization reaction media. The polymerization reaction is preferably conducted under substantially anhydrous conditions. If desired, conventional chain terminators, catalysts, activators, and other polymerization additives may be employed.

The Formula I composition alone or in conjunction with other thermoplastic materials may be utilized in coating or adhesively binding or laminating substrates such as porous cellulosic materials (e.g., paper, cardboard, pasteboard, wood products, etc.) thermosetting and thermoplastic materials (e.g., films and sheets), synthetic and natural fabrics, metals, glass, rubbers, ceramics, etc. The adhesive or coating or laminating composition may be applied to any suitable substrate with Formula I composition being dissolved or dispersed in an appropriate volatile liquid phase (e.g., organic solvents or aqueous based vehicles) or as a molten mass. Laminated substrates can be prepared by applying adhesive compositions containing the Formula I composition between superposed layers of one or more materials and heat sealing the superposed layers together to provide a laminate thereof.

The following examples are merely illustrative and should not be construed as limiting the scope of the invention.

EXAMPLE I

I(A) PREPARATION OF MALEATED ALPHA-OLEFIN

In a 1-liter, three-neck flask equipped with a thermometer, reflux condenser, and stirrer, 168g (1 mole) of $C_{12}$ alpha-olefin (1-dodecene) and 98g (1 mole) of maleic anhydride are heated together at a temperature of 230°C. for 3 hours with continuous stirring. The maleated alpha-olefin is cooled and used in preparing the half ester product in step (B). The maleated alpha-olefin had an anilic number of 206 and contained 0.2% residual anhydride.

I (B) PREPARATION OF MALEATED ALPHA-OLEFIN HALF ESTER

One mole of maleated alpha olefin of I(A) (266g) was mixed with one mole of a nonylphenoxy polyoxyethylene ethanol[1] (1540g) in a 2 liter, three-neck flask fitted with a thermometer, stirrer, and reflux condenser. With moderate and continuous stirring, the mixture was heated and maintained at 150°C. for 3 hours. The resultant half-ester was cooled to room temperature and used in the solvent polymerization process in step (C) below. The melting point of the half-ester product was 38°–41°C.

1 — Hodag E-30 - a non-ionic surfactant manufactured and sold by Hodag Chemical Corporation having an average of about 30 polyoxyethylene units per molecule of surfactant.

I(C) PREPARATION OF THE HOT MELT ADHESIVE

In a hermetically sealed 1-liter, four-neck flask equipped with a thermometer, stirrer and reflux condenser, 35g of the half-ester reaction product of I(B) above was heated to 75°C. While maintaining the reaction media at 75°C. with continuous stirring, a monomer solution consisting of 190g vinyl acetate, 10g crotonic acid, 5g benzoyl peroxide and 5g propionaldehyde was then slowly metered into the flask over a four hour period at a rate of about 0.833 grams per minute. Upon completion of the vinyl acetate-crotonic acid monomer addition, the temperature was then raised to 140°C. and held for 2 hours to complete the polymerization reaction. With continuous mixing and while maintaining the polymerization media at 130°–140°C., a second monomer charge consisting of 50g vinyl toluene, 15g alpha-methyl styrene, 6g methacrylic acid and 5g t-butyl hydroperoxide catalyst were slowly metered into the polymerization flask over a 1 hour time interval (at 1.1 grams/min.). Upon completion of the termonomer charge, the polymerization media was continuously mixed at 130°–140°C. for another hour. The polymerization media temperature was then raised and maintained at 170°C. with uniform mixing thereof for an additional hour. Residual monomer and catalyst were then stripped from the reaction product by vigorously mixing the polymerizate products at 170°C. in the presence of a nitrogen stream for 30 minutes. The resultant hot-melt adhesive was then removed from the flask at 170°C. and allowed to solidify under ambient conditions. The solidified hot-melt composition had a softening point of 191°F.[2]. The hot-melt composition had a viscosity of 2,650 cps (350°F. in a Brookfield Thermosel with a SC4-27 spindle at 10 rpm).

2 — Ring-and-ball softening point apparatus.

I(D) ADHESIVE LAMINATION OF PAPER STOCK

Strips of 50-pound kraft paper (1⅝ by 9 inch) were bonded together by applying the hot-melt adhesive composition (at 350°F.) to one end of the strip and manually folding the superimposing thereover the other end of the strip. The superimposed layers were then manually compressed together to provide a heat-sealed laminate thereof. The adhesive bonds were approximately between 1 to 2 mils in thickness covering approximately a one square inch area. The hot-melt composition possessed excellent tack and adhesive characteristics with fast setting properties. The folded test strips adhesively bonded together at their outer extremities were then cut at the center fold. Tear-seal tests upon the laminates were then conducted by gripping the free ends of the strips and manually pulling slowly in opposite directions perpendicular to the adhesive bond. The tear-seal tests indicated excellent adhesive bonding of kraft paper with the resultant tear strips therefrom evincing a dense paper fiberous layer without any concomitant evidence of adhesion failure of the hot-melt. The test strips were stable against failure upon aging and storage for prolonged periods of time at sub-zero and tropical temperatures under both arid and humid conditions. The adhesive bonds were stable against failure when exposed to flushing with water at neutral and acidic pH's. The adhesive bonds were converted to a water-soluble form by immersing the test strips into aqueous sodium hydroxide solutions (0.3% sodium hydroxide).

I(E) REPULPING AND RECYCLING OF PAPER STOCK CONTAMINATED WITH HOT-MELT ADHESIVE

Three-tenths (0.3g) of a molten hot-melt adhesive composition I(C) was separately and uniformly applied as a thin coating upon about 1% of the surface of 15 gram test samples of bleached and unbleached 50-pound kraft paper stocks. The coated paper stocks were then allowed to cool to room temperature and then cut into ½ inch squares. About 15 parts by weight of paper squares were then introduced into a standard alkaline repulping solution (250 parts by weight of 0.3% sodium hydroxide solution) and mixed with a gentle rolling action for 15 minutes at 185°F. This aqueous mixing removed the alkali-soluble adhesive composition from the pulp. The resultant paper pulp stock was then converted into paper sheets via a Noble-Wood handsheet machine half full of water. The paper stocks were agitated until uniformly dispersed therein and then made into handsheets. The resultant handsheets were sandwiched between two blotters and couched with a stainless steel roller. Each paper sheet was removed from the blotter and passed through a felt covered drum drier at 200°F. (2 minute drying time). Each dry paper sheet was then removed from the drum drier. The resultant recycled paper sheets were of uniform, high grade paper quality and essentially free from sticky, thermoplastic or non-fibrous material.

EXAMPLE II

Via the methodology of Example I(A), I(B) and I(C) several polymerization products were prepared by employing different maleated alphaolefin-monohydric alcohol reaction products as a polymerization solvent media. In runs 1–3, the Formula I half-ester composition was a maleated $C_{16}$ alpha-olefin reacted with a nonylphenoxypolyoxyethylene ethanol having an average of 8 ethylene oxide units per molecule. For Runs 4–9, the monohydric alcohol Formula I composition half-ester reaction product was obtained by reacting a maleated $C_{16}$ alpha-olefin with a nonylphenoxypolyoxyethyleneoxide having an average of 6 ethylene oxide units per molecule. In runs 10–19 the half-ester Formula I reaction product was obtained by reacting a maleated $C_{12}$ alpha-olefin with a nonylphenoxypolyoxyethylene ethanol which had an average of 30 ethylene oxide units per molecule. These half-ester products were prepared in accordance with I(A) and I(B) of Example I. On a parts by weight basis, 0.7, 1.0, 0.5, 0.1, 0.2 di t-butyl peroxide catalyst was respectively employed in runs 1, 2, 3, 4 and 5 with 2.0 parts by weight being employed in runs 6–9. For Runs 10–16 and 18–19 there was respectively employed 4, 10, 5, 4, 10, 10, 10, 3 and 10 parts by weight benzoyl peroxide and 0.5 azodiisobutyronitrile for Run 17. These polymerization reactions were conducted at a temperature between 130°–150°C. The parts by weight of half-ester products and parts by weight of copolymerized ethylenical monomers employed in the polymerization reaction are tabulated in Table I. The softening points and viscosity characteristics (at 350°F.) of the resultant hot-melt formulation are tabulated for each of the Runs.

TABLE I

| Run No. | Half-ester (pbw) | Styrene (pbw) | Acrylate (pbw) | Methacrylic Acid (pbw) | Other Monomers (pbw) | Softening Point[11] | Viscosity (cps)[12] |
|---|---|---|---|---|---|---|---|
| 1 | 150 | 200 | | 50 | | 212°F. | 21,250 |
| 2 | 150 | 120 | | 30 | | 187°F. | 8,750 |
| 3 | 150 | 90 | LMA[4] (30) | 30 | | 178°F. | 10,250 |
| 4 | 120 | 154 | EHA[5] (20) | 26 | | 178°F. | 6,600 |
| 5 | 320 | 280 | | 60 | ISOP[6] (60) | 174°F. | 3,100 |
| 6 | 100 | 140 | EA[7] (30) | 30 | | 210°F. | 9,500 |
| 7 | 100 | 140 | BA[8] (30) | 30 | | 198°F. | 4,875 |
| 8 | 100 | 130 | EMA[9] (40) | 30 | | 205°F. | 5,940 |
| 9 | 100 | 130 | BMA[10] (40) | 30 | | 192°F. | 3,560 |
| 10 | 50 | 170 | | 30 | | 226°F. | 17,000 |
| 11 | 75 | 150 | | 20 | ISOP[6] (30) | 176°F. | 1,850 |

| Run No. | Half-ester (pbw) | Styrene (pbw) | Vinyl Toluene (pbw) | Methacrylic Acid (pbw) | α-methyl Styrene (pbw) | Other Monomers (pbw) | Softening Point[11] | Viscosity (cps)[12] |
|---|---|---|---|---|---|---|---|---|
| 12 | 50 | 100 | 75 | 25 | | | 239°F. | 30,000 |
| 13 | 50 | 120 | | 25 | 25 | ISOP[6] (30) | 214°F. | 13,875 |
| 14 | 50 | | 175 | 25 | | | 240°F. | 10,375 |
| 15 | 50 | | 145 | 25 | | ISOP[6] (30) | 208°F. | 3,750 |
| 16 | 25 | 125 | | 25 | 50 | | 264°F. | 17,875 |

| Run No. | Half-ester (pbw) | Vinyl Acetate | Crotonic Acid (pbw) | Softening Point[11] | Viscosity (cps)[12] |
|---|---|---|---|---|---|
| 17 | 50 | 210 | 10 | 180°F. | 6,900 |
| 18 | 50 | 185 | 15 | 172°F. | 3,500 |
| 19 | 30 | 247 | 13 | 203°F. | 3,375 |

[4] - Lauryl methacrylate
[5] - Ethylhexyl acrylate
[6] - Isoprene
[7] - Ethyl acrylate
[8] - Butyl acrylate
[9] - Ethyl methacrylate
[10] - Butyl methacrylate
[11] - Ring-and-ball method
[12] - Brookfield Thermosel at 350°F. with SC4-27 spindle at 10 rpm

EXAMPLE III

Two-stage polymerization processes were conducted in accordance with the process of Example I(C) employing 50 parts by weight of the I(B) half-ester product. In Runs 20–22 a conventional chain terminator (e.g., propionaldehyde) for the copolymer polymerization reaction was not employed. In Runs 20–22, the initial monomer charge was 190 parts by weight vinyl acetate and 10 parts by weight crotonic acid with benzyl peroxide being employed as a catalyst in both the first and second stage polymerization reactions. The second stage polymerization charge, the softening and viscosity characteristics of the resultant polymerization products are delineated below.

| Run No. | Second-Stage Monomer Charge (pbw) | Softening Point[11] | Viscosity (cps)[12] |
|---|---|---|---|
| 20 | Styrene (36) Isoprene (8) Methacrylic Acid (6) | 225°F. | 28,750 |
| 21 | Vinyl Toluene (36) Isoprene (8) Methacrylic Acid (6) | 205°F. | 25,000 |
| 22 | Vinyl Toluene (20) Methyl Styrene (7) Isoprene (6) Methacrylic Acid (4.5) | 202°F. | 10,725 |

The viscosity of the Runs 20–22 hot-melts are greater than those of Example I(C) due to the relatively higher molecular weight of the first stage polymerization products. In Run 22, the 7 parts by weight alpha-methyl styrene functions as a chain terminator in the second stage polymerization reaction which resulted in a lower molecular weight polymer with a concomitant low hot-melt viscosity comparative to those of Runs 20 and 21. Other conventional chain terminators or transfer agents such as octyl, hexyl and n-dodecyl mercaptans, monothioglycerol, t-dodecyl mercaptan, thiophenol, diethyldisulfide, mercaptoethanol, etc., may also be used under the appropriate polymerization conditions to regulate the polymers molecular weight. The high proportion of half-ester product to other thermoplastic materials in the hot-melt formulation of Run 22 also contributed to this lower viscosity. By employing a conventional chain terminator and thereby regulating the polymer molecular weight and the amount of half-ester product hot-melt adhesives of a viscosity of the magnitude of the I(C) hot-melt can be prepared.

EXAMPLE IV

Hot-melt adhesive compositions were prepared by blending a molten mass of the I(B) half-ester and commercially available thermoplastic solids. The formulation of these hot-melts and resultant softening point and viscosity characteristics thereof are tabulated in Table II.

TABLE II

| Run No. | Half-Ester (pbw) | Thermoplastic (pbw) | Softening Point[11]-°F. | Viscosity (cps)[12] |
|---|---|---|---|---|
| 23 | 4 | Vinac 516[13] (15) | 205 | 15,600 |
| 24 | 2 | Vinac 516[13] (10) | 226 | 50,000 |
| 25 | 2 | Vinac 310[13] (15) | 194 | 17,000 |
| 26 | 3 | Jonacryl 67[14] (10) | 176 | 1,400 |

TABLE II-continued

| Run No. | Half-Ester (pbw) | Thermoplastic (pbw) | Softening Point[11]-°F. | Viscosity (cps)[12] |
|---|---|---|---|---|
| 27 | 5 | EAA 9500[15] (6) | 198 | 3,125 |

[13] - Vinac 516 and Vinac 310 are vinylacetate-crotonic acid copolymers manufactured and distributed by Air Products and Chemicals, Inc.
[14] - Jonacryl 67 is a styrene-acrylic acid copolymer manufactured and distributed by S. C. Johnson & Sons, Inc.
[15] - EAA 9500 is an ethylene-acrylic acid copolymer manufactured and distributed by Union Carbide Corporation As evident from the aforementioned Examples, the half-ester additives of this invention are compatible with thermoplastic materials obtained by polymerizing, in general, ethylenically unsaturated monomers.

Since many embodiments of this invention may be made and since many changes may be made in the embodiments described, the foregoing is interpreted as illustrative and the invention is defined by the claims appended hereafter.

What is claimed is:

1. A composition of the formula $$\left[ \begin{array}{c} R-CH=CH-CH_2-CH-\overset{O}{\underset{\|}{C}}- \\ CH_2-\overset{O}{\underset{\|}{C}}- \end{array} \right] \begin{array}{l} \leftarrow(OM)_1 \\ \\ \leftarrow(O+(CH_2)_d-O-(CH_2)_e-O+R^1)_f \end{array} \quad (I)$$

wherein R and $R^1$ represent hydrocarbyl groups, $d$ and $e$ represent repeating alkylene units of 1 to 5 carbon atoms inclusive, $f$ is an integer having an average value of about 2 to about 1,000 and M is a cation.

2. The composition of claim 1 wherein OM consists essentially of a hydroxyl group.

3. The composition of claim 2 wherein $d$ and $e$ represent methylene groupings of 2 to 3 carbon atoms inclusive and the composition contains an average of about 5 to about 100 polyalkyleneoxide units per molecule.

4. The composition according to claim 3 wherein $R^1$ represents an A—$(R^2)_g$ group with A being a phenylene or phenenyl group and $R^2$ is an alkyl group of 7 to 15 carbon atoms inclusive and $g$ is an integer having a value of 1 or 2 and R is an alkyl group having from about 5 to about 30 carbon atoms inclusive.

5. The composition of claim 4 wherein A—$(R^2)_g$ group is nonylphenyl with $d$, $e$ and $f$ representing from about 20 to about 40 repeating ethyleneoxide units.

6. The composition according to claim 1 wherein M is a member selected from the group consisting of an alkaline metal, hydrogen and a nitrogen base.

7. The composition according to claim 6 wherein $R^1$ represents an A—$(R^2)_g$ group with A being a phenylene or phenenyl group and $R^2$ an alkyl group of 7 to 15 carbon atoms inclusive and $g$ is an integer having a value of 1 to 2 and R is an alkyl group having from about 5 to about 30 carbon atoms inclusive and $f$ is an integer of about 10 to about 20.

8. In a hot-melt adhesive composition containing a blend of thermoplastic substances which are suitably adapted to be converted to a molten mass by thermal treatment thereof and deposited upon a substrate and adhesively bound to a substrate upon cooling to a temperature below the melting point of the hot-melt adhesive composition, the improvement which comprises incorporating into the hot-melt adhesive composition at least 0.25% of the total hot-melt composition weight, a hot-melt additive represented by the structural formula:

$$\left[ \begin{array}{c} R-CH=CH-CH_2-CH-\overset{O}{\underset{\|}{C}}- \\ CH_2-\overset{O}{\underset{\|}{C}}- \end{array} \right] \begin{array}{l} \leftarrow(OM)_1 \\ \\ \leftarrow(O+(CH_2)_d-O-(CH_2)_e-O+R^1)_f \end{array} \quad (I)$$

wherein R and $R^1$ represent hydrocarbyl groups, $d$ and $e$ represent repeating alkylene units of 1 to 5 carbon atoms inclusive, $f$ is an integer having an average value of about 2 to about 1,000 and M is a cation.

9. The hot-melt composition according to claim 8 wherein the weight ratio of hot-melt additive to thermoplastic polymeric material (exclusive of the hot-melt additive) ranges from about 1:19 to about 19:1.

10. The hot-melt composition according to claim 9 wherein the OM group consists essentially of a hydroxyl group.

11. The hot-melt composition according to claim 10 wherein $R^1$ represents an A—$(R^2)_g$ group with A being a phenylene or phenenyl group and $R^2$ is an alkyl group of 7 to 15 carbon atoms inclusive, $g$ is an integer having a value of 1 or 2, R is an alkyl group having from about 5 to about 30 carbon atoms inclusive and $d$, $e$ and $f$ represents from about 5 to about 50 repeating ethyleneoxide units.

12. The hot-melt composition according to claim 11 wherein $R^2$ is an alkyl group of 7 to 12 carbon atoms inclusive and R is an alkyl group of 7 to 15 carbon atoms inclusive and the hot-melt additive contains an average of about 20 to about 40 repeating ethyleneoxide units.

13. The composition according to claim 12 wherein the hot-melt composition contains from about 4 to about 9 parts by weight of thermoplastic material (exclusive of the hot-melt additive) for each part by weight hot-melt additive.

14. The hot-melt composition according to claim 9 wherein M is at least one cation selected from the group consisting of an alkaline metal, hydrogen and a nitrogen base.

15. The hot-melt composition according to claim 14 wherein the hot-melt contains from about 3 to about 15 parts by weight of polymerized ethylenically unsaturated monomers for each part by weight of hot-melt additive.

16. The composition of claim 15 wherein $R^1$ represent an alkylphenyl group in which the alkyl group contains from 7 to 15 carbon atoms inclusive, d, e and f represent an average of about 20 to about 40 repeating ethyleneoxide units and R is an alkyl group containing from 8 to 15 carbon atoms inclusive.

17. The composition according to claim 16 wherein OM consists essentially of a hydroxyl group.

18. A method for coating substrates which comprises applying to the substrate a coating composition containing on a non-volatile solids basis at least 0.25% by weight of a coating additive represented by the formula:

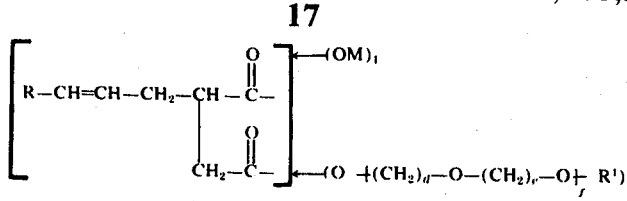

wherein R and R¹ represent hydrocarbyl groups, $d$ and $e$ represent repeating alkylene units of 1 to 5 carbon atoms inclusive, $f$ is an integer having an average value of about 2 to about 1,000 and M is a cation.

19. A method for laminating substrates together with the composition of claim 1, said method comprising applying a laminating formulation containing the composition of claim 1 to a lamina and superimposing another lamina thereon to provide a laminate thereof.

20. The laminated product of claim 19.

* * * * *

UNITED STATES PATENT AND TRADEMARK OFFICE
CERTIFICATE OF CORRECTION

PATENT NO. : 3,968,310
DATED : July 6, 1976
INVENTOR(S) : James K. Stowell

It is certified that error appears in the above–identified patent and that said Letters Patent are hereby corrected as shown below:

Column 1, line 29, for "in" read ---by---
Column 2, line 8, for "hot-melt hot-mel" read ---water-insoluble, hot-melt---
Column 8, line 39, for "unsaurated" read ---unsaturated---

Signed and Sealed this

Fourth Day of January 1977

[SEAL]

Attest:

RUTH C. MASON
Attesting Officer

C. MARSHALL DANN
Commissioner of Patents and Trademarks